US009480748B2

(12) United States Patent
Saint-Lu et al.

(10) Patent No.: US 9,480,748 B2
(45) Date of Patent: Nov. 1, 2016

(54) MUCOADHESIVE PARTICULATE FORMULATION FOR INDUCING ANTIGEN-SPECIFIC IMMUNE TOLERANCE

(71) Applicant: STALLERGENES S.A., Antony (FR)

(72) Inventors: Nathalie Saint-Lu, Antony (FR); Alain Razafindratsita, Antony (FR); Sophie Tourdot, Paris (FR); Philippe Moingeon, Antony (FR); Laurence Van Overtvelt, Massy (FR)

(73) Assignee: STALLERGENES, Antony (FR)

( * ) Notice: Subject to any disclaimer, the term of this patent is extended or adjusted under 35 U.S.C. 154(b) by 0 days.

(21) Appl. No.: 14/088,168

(22) Filed: Nov. 22, 2013

(65) Prior Publication Data

US 2014/0079795 A1 Mar. 20, 2014

Related U.S. Application Data

(62) Division of application No. 12/993,563, filed as application No. PCT/EP2009/056158 on May 20, 2009, now abandoned.

(30) Foreign Application Priority Data

May 20, 2008 (EP) .................................... 08305182

(51) Int. Cl.

| | |
|---|---|
| ***A01N 25/26*** | (2006.01) |
| ***A01N 25/28*** | (2006.01) |
| ***A61K 9/54*** | (2006.01) |
| ***A61K 9/62*** | (2006.01) |
| ***A61K 9/64*** | (2006.01) |
| ***A61K 39/35*** | (2006.01) |
| ***A61K 39/36*** | (2006.01) |
| ***A61K 47/36*** | (2006.01) |
| ***A61K 9/00*** | (2006.01) |
| ***A61K 9/16*** | (2006.01) |
| ***A61K 9/51*** | (2006.01) |
| ***A61K 9/14*** | (2006.01) |
| *A61K 39/00* | (2006.01) |

(52) U.S. Cl.

CPC ............... *A61K 47/36* (2013.01); *A61K 9/006* (2013.01); *A61K 9/146* (2013.01); *A61K 9/1652* (2013.01); *A61K 9/5161* (2013.01); *A61K 39/35* (2013.01); *A61K 2039/542* (2013.01); *A61K 2039/55583* (2013.01)

(58) Field of Classification Search

None

See application file for complete search history.

(56) References Cited

U.S. PATENT DOCUMENTS

| | | | | |
|---|---|---|---|---|
| 4,939,239 A * | 7/1990 | Matsuhashi ........ | A61K 47/4823 424/185.1 |
| 5,840,341 A | 11/1998 | Watts | |
| 6,475,995 B1 | 11/2002 | Roy et al. | |
| 8,420,095 B2 * | 4/2013 | Jensen-Jarolim .... | A61K 9/1647 424/184.1 |
| 2004/0234614 A1 | 11/2004 | Strong | |
| 2007/0275079 A1 * | 11/2007 | Jensen-Jarolin ..... | A61K 9/1647 424/491 |
| 2008/0014281 A1 | 1/2008 | Shibata et al. | |
| 2009/0270347 A1 * | 10/2009 | Strong ................ | A61K 9/0043 514/55 |
| 2010/0150960 A1 | 6/2010 | Schlom et al. | |

FOREIGN PATENT DOCUMENTS

| | | |
|---|---|---|
| WO | WO 96/05810 | 2/1996 |
| WO | WO 02/34287 | 5/2002 |
| WO | WO 2008/053192 | 5/2008 |

OTHER PUBLICATIONS

Sato et al. 'Clinical studies in oral allergen-specific immunotherapy: differences among allergens.' Int. Arch. Allergy Immunol. 164(1):1-9, 2014.*

Zolkipli et al. 'Randomized controlled trial of primary prevention of atopy using house dust mite allergen oral immunotherapy in early childhood.' J. Allerg. Clin. Immuno.. 136(6):1541-1547, 2015.*

Blumenthal et al, "Definition of an Allergen," *Allergens and Allergen Immunotherapy*, Ed. R. Lockey, S. Bukantz and J. Bousquet, New York: Marcel Decker, pp. 37-50 (2004).

Canonica et al., "Sublingual immunotherapy in the treatment of adult allergic rhinitis patients," *Allergy*, 61(81):20-23 (2006).

Chew et al., "Chitosan nanoparticles containing plasmid DNA encoding house dust mite allergen, Der p 1 for oral vaccination in mice," *Vaccine*, 21:2720-2729 (2003).

Cunningham et al., "Sublingual immunotherapy to inhalant allergen sensitization and the effect of chitosan," *World Allergy Congress*, 116 (Abstract) (2007).

Hall et al., "Kinetics and mode of peptide delivery via the respiratory mucosa determine the outcome of activation versus TH2 immunity in allergic inflammation of the airways," *J. Allergy Clin. Immunol.*, 110:883-890 (2002).

Hamelmann et al., "Noninvasive Measurement of Airway Responsiveness in Allergic Mice Using Barometric Plethysmography," *Am. J. Respir. Crit. Care Med.*, 156:766-775 (1997).

Jayakumar et al., "Sulfated chitin and chitosan as novel biomaterials," *Intl. J. Biol. Macromol.*, 40:175-181 (2007).

(Continued)

*Primary Examiner* — Nora Rooney

(74) *Attorney, Agent, or Firm* — Browdy and Neimark, P.L.L.C.

(57) ABSTRACT

The present disclosure relates to a mucoadhesive composition, adapted for preventing and/or treating a pathological reaction of the immune system of an individual, by inducing a specific tolerance towards at least one antigen involved in said pathological reaction, comprising chitosan particles loaded with said at least one antigen involved in the pathological reaction, wherein the size of the loaded chitosan particles is of more than 800 nm.

10 Claims, 10 Drawing Sheets

(56) References Cited

OTHER PUBLICATIONS

Kinnunen et al, "Potential/of/an altered peptide ligand of lipocalin allergen Bos d 2 for peptide immunotherapy," *J. Allergy Clin. Immunol.*, 119(4): 965-972 (2007).
Ko et al., "Preparation and characterization of chitosan microparticles intended for controlled drug delivery," *Intl. J. Pharm.*, 249:165-174 (2002).
Kumar et al., "Chitosan IFN-γ-pDNA Nanoparticle (CIN) Therapy for Allergic Asthma," *Genet. Vaccines Ther.*, 1:3 (2003).
Moingeon et al., "Immune mechanisms of allergen-specific sublingual immunotherapy," *Allergy*, 61:151-165 (2006).
Novak et al., "Dendritic cells as regulators of immunity and tolerance," *J. Allergy Clin. Immunol.*, 121:S370-374 (2008).
O'Hagan et al., "Recent Advances in the Discovery and Delivery of Vaccine Adjuvants," *Nat. Rev. Drug Discov.*, 2:727-735 (2003).
Porporatto et al., "Early events associated to the oral co-administration of type II collagen and chitosan: induction of anti-inflammatory cytokines," *Intl. Immunol.*, 16(3): 433-441 (2004).
Razafindratsita et al., "Improvement of sublingual immunotherapy efficacy with a mucoadhesive allergen formulation," *J. Allergy Clin. Immunol.*, 120:278-285 (2007).
Roy et al., "Oral gene delivery with chitosan-DNA nanoparticles generates immunologic protection in a murine model of peanut allergy," *Nature Medicine*, 5(4):387-391 (1999).
Schöll et al., "Review of novel particulate antigen delivery systems with special focus on treatment of type I allergy," *J. Controlled Release*, 104:1-27 (2005).
van der Lubben et al, "Chitosan microparticles for oral vaccination: preparation, characterization and preliminary in vivo uptake studies in murine Peyer's patches," *Biomaterial*, 22:687-694 (2001).
Veronesi et al., "The Surface Charge of Visible Particulate Matter Predicts Biological Activation in Human Bronchial Epithelial Cells," *Toxicol. Appl. Pharmacol.*, 178:144-154 (2002).
Wilson et al., "Sublingual immunotherapy for allergic rhinitis: systematic review and meta-analysis," *Allergy*, 60:4-12 (2005).
Int'l Search Report & Written Opinion issued in application No. PCT/EP2009/056158 (2009).

* cited by examiner

MUCOADHESIVE PARTICULATE FORMULATION FOR INDUCING ANTIGEN-SPECIFIC IMMUNE TOLERANCE

CROSS REFERENCE TO RELATED APPLICATIONS

This application is a Divisional of copending U.S. application Ser. No. 12/993,563, filed Mar. 8, 2011, which is a U.S. nationalization under 35 USC §371 of International Application No. PCT/EP2009/056158, filed May 20, 2009, which claims priority to European Patent Application No. EP 08305182.1, filed May 20, 2008. The disclosures set forth in the referenced applications are incorporated herein by reference in their entireties.

FIELD OF THE DISCLOSURE

The present disclosure relates to a mucoadhesive formulation for inducing antigen-specific immune tolerance and to methods using the same.

BACKGROUND OF THE DISCLOSURE

Sublingual immunotherapy (SLIT) is a non-invasive and efficacious treatment of type I respiratory allergies (Canonica & Passalacqua *Allergy* 2006; 61:20-23, Wilson et al. *Allergy* 2005; 60:4-12). However, it remains to be optimized, with respect for example to treatment duration and administration schedules. In this context, appropriate delivery systems are to be identified to improve tolerance induction via the sublingual route. Mucoadhesive and/or particulate formulations appear to be particularly promising with the aim of (i) enhancing contact duration with the mucosa, thus improving the amount of allergen penetrating the sublingual mucosa, and (ii) targeting antigen-presenting cells (APCs) within the oral mucosa, which are prone to induce tolerance (Moingeon et al. *Allergy* 2006; 61:151-165, Novak & Bieber *J Allergy Clin Immunol* 2008; 121:S370-4).

Chitosan is a polycationic polysaccharide derived by deacetylation of chitin. Chitosan naturally occurs in crustaceans, insects, mushrooms and microorganisms. It is biodegradable, biocompatible, well tolerated and shows no irritating or sensitizing properties, consequently it has been approved by the FDA for human utilization (Jayakumar et al. *Int J Bio Macromolecules* 2007; 40:175-181).

Chitosan-based products are already in use in the medical, cosmetic, health supplement and environmental industries. Most particularly, among the possible forms of chitosan-based polymers, chitosan particles are interesting delivery system candidates to target the antigen to mucosal DCs because of their polycationic nature, which is responsible for their mucoadhesiveness, and because of their particulate form, which facilitates uptake by APCs and transport to secondary lymphoid organs (O'Hagan & Valiante *Nat Rev Drug Discov* 2003; 2:727-735). In the field of antigen-specific tolerance induction, a few studies have investigated the effect of chitosan particles, mostly as a gene delivery system via the intranasal or oral route (Roy et al. *Nat Med* 1999; 5:387-391; Kumar et al. *Genet Vaccines Ther* 2003; 1:3; Chew et al. *Vaccine* 2003; 21:2720-2729)). As regards peptide delivery using chitosan, no sound teachings can be derived from prior art concerning the potential of chitosan as a delivery system. Thus, Porporatto et al. *Int Immunol* 2004; 16:433-441 report that the oral administration of low molecular weight chitosan in association with type II collagen promotes an anti-inflammatory environment early after feeding. Hall et al. *J. Allergy Clin Immunol* 2002; 100:883-89 show that intranasal administration of chitosan in association with an allergen reduces airway inflammation. Conversely, Cunningham et al. *World Allergy Congress* 2007 116, (Abstr) indicate that sublingual administration of an allergen in association with chitosan leads to a non-specific reduction of lung inflammation, which is not superior to the one observed when the allergen is administered alone.

SUMMARY OF THE DISCLOSURE

The present disclosure arises from the unexpected finding, by the inventors, that high-size chitosan particles had an enhanced ability to induce antigen-specific immune tolerance when compared with particles of chitosan of lower size.

Thus, the present disclosure relates to a mucoadhesive composition adapted for preventing and/or treating a pathological reaction of the immune system of an individual in particular by inducing a specific tolerance towards at least one antigen involved in said pathological reaction, comprising chitosan particles loaded with said at least one antigen involved in the pathological reaction, wherein the size, or diameter, of the loaded chitosan particles is of more than 800 nm.

The present disclosure also relates to an immunotherapeutic composition comprising an above-defined mucoadhesive composition in association with a pharmaceutically acceptable carrier.

The present disclosure also relates to the mucoadhesive composition as defined above, or the immunotherapeutic composition as defined above, in its application as a medicament, or to the use of the mucoadhesive composition as defined above, or the immunotherapeutic composition as defined above, for the manufacture of a medicament, wherein the medicament is intended for preventing and/or treating a pathological reaction of the immune system of an individual, in particular by inducing a specific tolerance towards at least one antigen involved in said pathological reaction. The present disclosure further relates to the mucoadhesive composition as defined above, or the immunotherapeutic composition as defined above, for use, in particular as a medicament, for the prevention and/or treatment of a pathological reaction of the immune system of an individual, in particular by inducing a specific tolerance towards at least one antigen involved in said pathological reaction.

The present disclosure also relates to a method for preventing or treating a pathological reaction of the immune system in an individual, in particular by inducing a specific tolerance towards at least one antigen involved in said pathological reaction, comprising administering to said individual a prophylactically or therapeutically effective quantity of a mucoadhesive composition as defined above.

DETAILED DESCRIPTION OF THE DISCLOSURE

Antigen

As intended herein an "antigen involved in a pathological reaction of the immune system of an individual" relates to a compound which is liable to induce a reaction of the immune system specifically directed against it and which is responsible for the onset or the maintaining of an immune reaction against the individual, in particular against cells, tissues or organs of the individual.

The antigen may be of any type. In particular, it can be a protein, a polypeptide or a peptide, a carbohydrate, a lipid, a nucleic acid, such as DNA or RNA, or a virus, in particular a recombinant virus. However, it is preferably a protein, a polypeptide or a peptide. As intended herein, "protein" will be understood to encompass protein, polypeptide and peptide.

The antigen may be selected from the group consisting of an allergen, an auto-antigen and a graft-specific antigen.

In a preferred embodiment, the antigen is an allergen. An "allergen" is defined as a substance, usually a protein, which elicits the production of IgE antibodies in predisposed individuals. Similar definitions are presented in the following references: Clin. Exp. Allergy, No. 26, pp. 494-516 (1996); Mol. Biol. of Allergy and Immunology, ed. R. Bush, Immunology and Allergy Clinics of North American Series (August 1996).

Preferably the antigen is a protein allergen, i.e. any amino acid chain likely to trigger an allergic response, including short peptides of about 6 to 20 aminoacids, polypeptides, or full proteins.

Non limitative examples of allergens include pollen allergens (such as tree-, herb, weed-, and grass pollen allergens), insect allergens (such as inhalant, saliva and venom allergens, e.g., cockroach and midges allergens, hymenopthera venom allergens), mite allergens, animal hair and dandruff allergens (from e.g. dog, cat, horse, rat, mouse etc.), and food allergens.

For instance, the protein allergen may be selected from the group consisting of a protein allergen of the genus *Dermatophagoides*; a protein allergen of the genus *Felis*; a protein allergen of the genus *Ambrosia*; a protein allergen of the genus *Lolium*; a protein allergen of the genus *Cryptomeria*; a protein allergen of the genus *Alternaria*; a protein allergen of the genus *Alder*; a protein allergen of the genus *Betula*; a protein allergen of the genus of *Blomia*; a protein allergen of the genus *Quercus*; a protein allergen of the genus *Olea*; a protein allergen of the genus *Artemisia*; a protein allergen of the genus *Plantago*; a protein allergen of the genus *Parietaria*; a protein allergen of the genus *Canine*; a protein allergen of the genus *Blattella*; a protein allergen of the genus *Apis*; a protein allergen of the genus *Cupressus*; a protein allergen of the genus *Thuya*; a protein allergen of the genus *Chamaecyparis*; a protein allergen of the genus *Periplaneta*; a protein allergen of the genus *Agropyron*; a protein allergen of the genus *Secale*; a protein allergen of the genus *Triticum*; a protein allergen of the genus *Cynorhodon*; a protein allergen of the genus *Juniperus*; a protein allergen of the genus *Dactylis*; a protein allergen of the genus *Festuca*; a protein allergen of the genus *Poa*; a protein allergen of the genus *Avena*; a protein allergen of the genus *Holcus*; a protein allergen of the genus *Anthoxanthum*; a protein allergen of the genus *Arrhenatherum*; a protein allergen of the genus *Agrostis*; a protein allergen of the genus *Phleum*; a protein allergen of the genus *Phalaris*; a protein allergen of the genus *Paspalum*; and a protein allergen of the genus *Sorghum*.

Examples of various known protein allergens derived from some of the above-identified genus include: *Betula* (*verrucosa*) Bet v I; Bet v II; *Blomia* Blo t I; Blo t III; Blo t V; Blo t XII; *Cynorhodon* Cyn d I; *Dermatophagoides* (*pteronyssinus* or *farinae*) Der p I; Der p II; Der p III; Der p VII; Der f I; Der f II; Der f III; Der f VII; *Felis* (*domesticus*) Fel d I; *Ambrosia* (*artemiisfolia*) Amb a I.1; Amb a I.2; Amb a I.3; Amb a I.4; Amb a II; *Lollium* (*perenne*) Lol p I; Lot p II; Lol p III; Lot p IV; Lol p IX (Lol p V or Lol p Ib); *Cryptomeria* (*japonica*) Cry j I; Cry j II; *Canis* (*familiaris*) Can f I; Can f II; *Juniperus* (*sabinoides* or *virginiana*) Jun s I; Jun v I; *Juniperus* (*ashei*) Jun a I; Jun a II; *Dactylis* (*glomerata*) Dac g I; Dac g V; *Poa* (*pretensis*) *Poa* p I; Phl p I; Phl p V; Phl p VI and *Sorghum* (*halepensis*) Sor h I.

Food allergens may originate from milk and milk products, eggs, legumes (peanuts and soy), tree nuts, wheat, crustaceans, fish, and mollusks. In particular, food allergens may be ovalbumine or gluten.

In addition, similar to allergy, autoimmune diseases such as type I diabetes, multiple sclerosis, and rheumatoid arthritis are generally accepted as being the result of an antigen specific T cell mediated response against an antigen which in the case of autoimmune disease is an auto-antigen, i.e. an antigen that belongs to the body's own tissue. The same applies to the phenomenon of graft rejection, where the antigen belongs to the graft tissue, possibly coming from another individual or even from another animal species.

In another embodiment, the antigen is involved in an autoimmune disease or graft rejection.

A number of antigens (i.e. auto-antigens) have been found to cause symptoms in autoimmune diseases (i.e. auto-antigens such as insulin; myelin basic protein; rh factor; acetylcholine receptors; thyroid cell receptors; basement membrane proteins; thyroid proteins; ICA-69 (PM-1); glutamic acid decarboxylase (64K or 65K); proteolipid protein (PLP), myelin associated glycoprotein (MAG), Collagen (Type II), Heat Shock Protein and carboxypeptidase H) such as diabetes, rheumatoid arthritis, and multiple sclerosis.

Furthermore, graft-specific antigen may elicit a graft versus host disease which may lead ultimately to rejection of the graft.

Chitosan Particle

Chitosan is a polysaccharide constituted of units of N-acetyl-D-glucosamine and D-glucosamine, which units are linked together through β-1-6 linkages. Usually chitosan is produced by deacetylation of chitin, an homopolysaccharide of N-actetyl-D-glucosamine units linked together through β-1-6 linkages. Chitin is notably found in crustacean shells or vegetal sources.

Preferably, the acetylation percentage of chitosan polysaccharides present in the chitosan particle of the disclosure, that is the number of acetylated units in a polysaccharide with respect to the total number of units in the polysaccharide, is lower than 25%.

Preferably, the chitosan particle of the disclosure is made of high molecular weight chitosan, that is chitosan polysaccharides which mean molecular weight is preferably higher than 300 kDa or which viscosity is preferably of at least 800 cP (wherein viscosity is preferably measured according to the well-known Brookfield method with a 1% solution of the chitosan polysaccharides in 1% acetic acid).

The size of the loaded chitosan particle is of more than 800 nm, and preferably ranges from 1 μm to 3 μm.

The zeta potential of the loaded chitosan particle is preferably of more than 2.5 mV, more preferably of from 6 mV to 9 mV, and most preferably of about 7.3 mV.

The zeta potential of a particle reflects the surface charge of the particle. It corresponds to the difference in electrical charge between the dispersion medium in which the particle is standing and the dense layer of ions which surrounds the particle. The zeta potential is notably defined by Veronesi et al. Toxicol Appl Pharmacol 2002; 178:144-154.

The size and the zeta potential of the loaded chitosan particle of the disclosure can be measured by any suitable method. Preferably, they are measured with the following apparatus: Zetasizer Nano ZS (Malvern, Worcestershire, UK).

The antigen can be loaded onto the chitosan particle of the disclosure according to any suitable method. However, the antigen is preferably cross-linked to the chitosan particle of the disclosure. Numerous well known methods for cross-linking the antigen to the chitosan particle are available to one of skill in the art depending of the nature of the antigen. Where the antigen is a protein, one can notably mention ionic cross-linking, for instance using tripolyphosphate or genipin, or chemical cross-linking, for instance using glutaraldehyde, NaOH, or ethylene glycol diglycidyl ether (e.g. as used by Ko et al. Int J Pharm 2002; 249:165-174).

By way of example, the loaded chitosan particle of the disclosure can be prepared by a method comprising:

dissolving high molecular weight chitosan (e.g. available from Sigma-Aldrich under reference 419419) in an aqueous acetic acid solution;

adding the antigen to the solution;

cross-linking the antigen to chitosan.

Immunotherapeutic compositions, medicaments and methods for preventing or treating a pathological reaction of the immune system in an antigen-specific manner As intended herein a "pathological reaction of the immune system of an individual" relates to an immune reaction which is targeted against tissues or cells of the organism which harbours said immune system.

Such a pathological reaction is in particular selected from the group consisting of allergy, such as asthma, autoimmune disease or graft rejection.

In the context of the disclosure allergy relates to asthma or to the allergies due to the above-defined allergens.

In the context of the disclosure an autoimmune disease in particular relates to Type I diabetes, multiple sclerosis, rheumatoid arthritis, and to the diseases due to the above-defined auto-antigens.

As intended herein the term "immunotherapeutic" relates to the capacity of a substance to prevent or to treat a pathological reaction of the immune system.

In the context of the disclosure, the terms "to treat", "treating" or "treatment", means reversing, alleviating, or inhibiting the course of a pathological reaction of the immune system or one or more symptoms thereof.

In the context of the disclosure, the terms "to prevent" or "preventing", means impeding the onset of a pathological reaction of the immune system or one or more symptoms thereof.

As used herein, the term "individual" preferably denotes a mammal, such as a rodent, a feline, a canine, and a primate. Preferably, an individual according to the disclosure is a human.

"Pharmaceutically" or "pharmaceutically acceptable" refer to molecular entities and compositions that do not produce an adverse, allergic or other untoward reaction when administered to an animal, or a human, as appropriate.

As used herein, "pharmaceutically acceptable carrier" includes any and all solvents, dispersion media, coatings, antibacterial and antifungal agents, isotonic and absorption delaying agents and the like. The use of such media and agents for pharmaceutical active substances is well known in the art. Except insofar as any conventional media or agent is incompatible with the loaded chitosan particles according to the disclosure, its use in the immunotherapeutic compositions, in the medicaments, or for implementing the methods for preventing or treating a pathological reaction of the immune system in an individual according to the disclosure is contemplated. Supplementary active ingredients can also be incorporated into the compositions.

It is thought that the particular immunotherapeutic properties of the loaded chitosan particle of the disclosure arise from its size and positive charge which, unexpectedly and particularly, favour uptake and processing of the antigen it is loaded with, by mucosal, in particular oromucosal, more particularly sublingual cells, such as dendritic cells, thereby favouring antigen-specific tolerance induction.

Moreover, the chitosan particle of the disclosure is mucoadhesive. Mucoadhesivity enables close and prolonged contact with a mucosa, in particular a mucosa of the oral cavity, and more particularly the sublingual mucosa, thereby enhancing-antigen specific tolerance induction.

Preferably, the loaded chitosan particle, the immunotherapeutic composition, or the medicament of the disclosure, is to be administered by the mucosal route, more preferably by the oromucosal route, and most preferably by the sublingual route. As such, the immunotherapeutic composition and the medicament are preferably formulated in a way adapted for such administration routes.

Mucosal administration denotes any administration method, wherein the formulation in part or in full comes into contact with a mucosa. Mucosa refers to the epithelial tissue that lines the internal cavities of the body. The mucosal surface may be selected from the group consisting of a nasal, buccal, oral, vaginal, ocular, auditory, pulmonary tract, urethral, digestive tract, and rectal surface.

Oromucosal administration comprises any administration method, wherein the formulation in part or in full comes into contact with the mucosa of the oral cavity and/or the pharynx of the patient.

Oromucosal administration includes in particular sublingual, perlingual (i.e. through the tongue mucosa) and oral administrations.

The loaded chitosan particles, the immunotherapeutic compositions or the medicaments according to the disclosure can be administered in various forms, such as dispersed forms, e.g. in suspensions or gels, or as dry forms, e.g. in powders, tablets, capsules, lyoc, or forms suitable to be administered in a metered-dosing device, In the frame of methods for preventing or treating pathological reactions of the immune system, the immunotherapeutic compositions or the medicaments, according to the disclosure may further comprise an adjuvant for enhancing antigen-specific tolerance induction. Any conventional or exploratory, synthetic or biological adjuvant for vaccination, including heat-labile enterotoxin (LT), cholera-toxin (CT), cholera toxin B subunit (CTB), polymerised liposomes, mutant toxins, probiotic bacteria, oligonucleotides, RNA, siRNA, DNA, lipids can be associated to the loaded chitosan particles according to the disclosure to enhance antigen-specific tolerance induction. For oromucosal administration, the adjuvants may be preferably a bacterium selected from a *Bifidobacterium* and a lactic acid bacterium, or a combination of a corticosteroid with vitamin D3 or any metabolite or analog of the latter.

In the frame of methods for preventing or treating pathological reactions of the immune system, the immunotherapeutic compositions or the medicaments, according to the disclosure, the administration regimen may be repeated for a period of less than 6 weeks to up to three years.

Furthermore prevention or treatment may be effected with a plurality of different antigens. This may be achieved either with one type of chitosan particle of the disclosure loaded with a plurality of antigens or with a plurality of chitosan particles of the disclosure containing one or more antigens each.

Preferably, in the frame of methods for preventing or treating pathological reactions of the immune system, in the immunotherapeutic compositions or the medicaments, according to the disclosure, the dose of allergen comprised in the loaded chitosan particles of the disclosure ranges from 0.1 μg to 100 mg.

The disclosure will be further illustrated in view of the following figures and examples.

OVA formulated in chitosan particles is well recognized by specific antibodies. Soluble OVA or high or medium MW chitosan-formulated OVA were detected by ELISA (inhibition test) using sera from OVA-immunized mice.

FIG. 2, FIG. 3, FIG. 4, FIG. 5 and FIG. 6

Both chitosan particles improve OVA uptake and processing by BMDCs, but only high MW chitosan particles improve OVA processing by oral DCs. For uptake studies, FITC-OVA or high MW chitosan-formulated FITC-OVA (FIG. 2) or medium MW chitosan-formulated FITC-OVA (FIG. 3) were incubated with BMDCs for 15, 60 or 240 min, at 37° C. or 4° C. For processing assays, DQ-OVA or high MW chitosan-formulated DQ-OVA or medium MW chitosan-formulated DQ-OVA were incubated with either BMDCs (FIGS. 4 and 5) or purified oral DCs (FIG. 6), at a final concentration of 10 μg/ml, for 3 h (BMDCs) or 1 h (oral DCs) at 37° C. or 4° C. Cells were then analysed usinga FC500 flow cytometer.

FIG. 7, FIG. 8, FIG. 9 and FIG. 10

Figure 7:
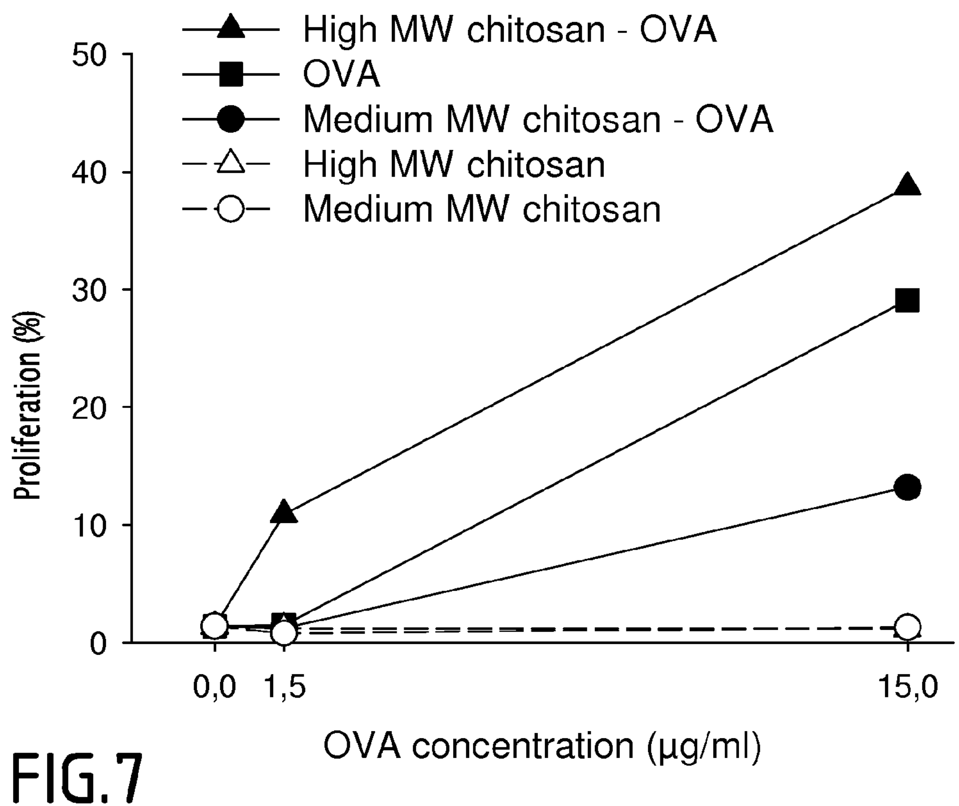
Figure 8:
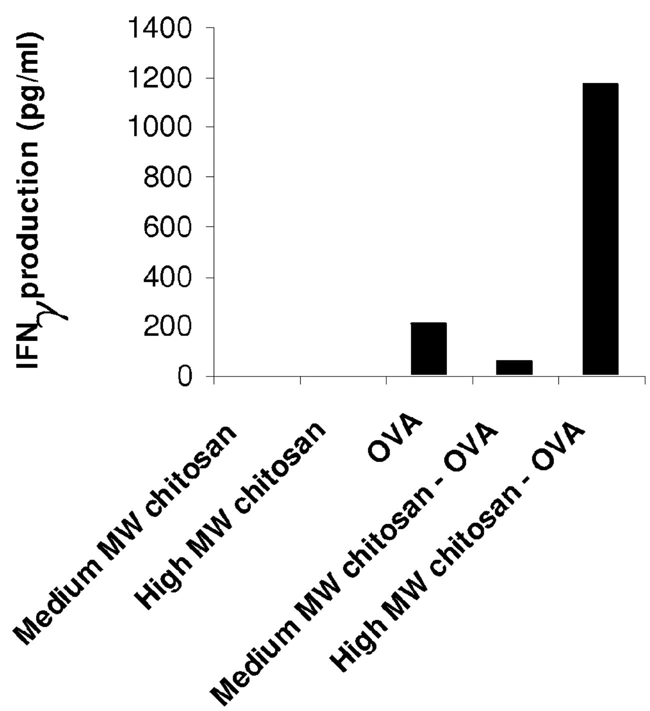
Figure 9:
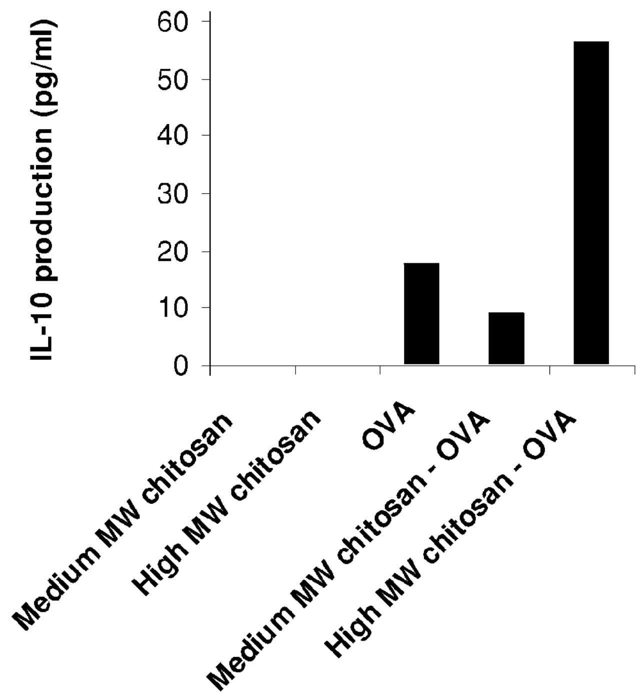

High MW chitosan particles increase in vitro T cell proliferation and IFN-γ/IL-10 secretions. OVA-specific CD4+ T lymphocytes from DO11.10 mice were labelled with CFSE and cocultured with BMDCs and either OVA (1.5 or 15 μg/ml), high MW or medium MW chitosan-formulated OVA (1.5 or 15 μg/ml), or the chitosan formulations alone. After 3 days, cells were harvested, stained with PE-KJ1.26 mAb, and CFSE content was analyzed in responder T cells using a FC500 flow cytometer (FIG. 7). IFN-γ (FIG. 8), IL-10 (FIG. 9), and IL-5 (FIG. 10) were measured by CBA assay in cell cultures supernatants corresponding to 15 μg/ml OVA concentrations.

FIG. 11

High MW chitosan particles enhance in vivo T cell priming in cervical LNs. Purified CFSE-labelled DO11.10 CD4+ T cells were adoptively transferred into BALB/c mice at day 0. Twenty-four hours later, mice were treated by the sublingual route with soluble OVA or chitosan-formulated OVA (high or medium MW). Control animals were treated with either sterile PBS or chitosan formulations alone. At day 10, cervical LNs were removed. Proliferating cells were detected by flow cytometry (representative data of 3 to 5 mice per group).

FIG. 12, FIG. 13, FIG. 14, FIG. 15, FIG. 16, FIG. 17, FIG. 18 and FIG. 19

Figure 12:
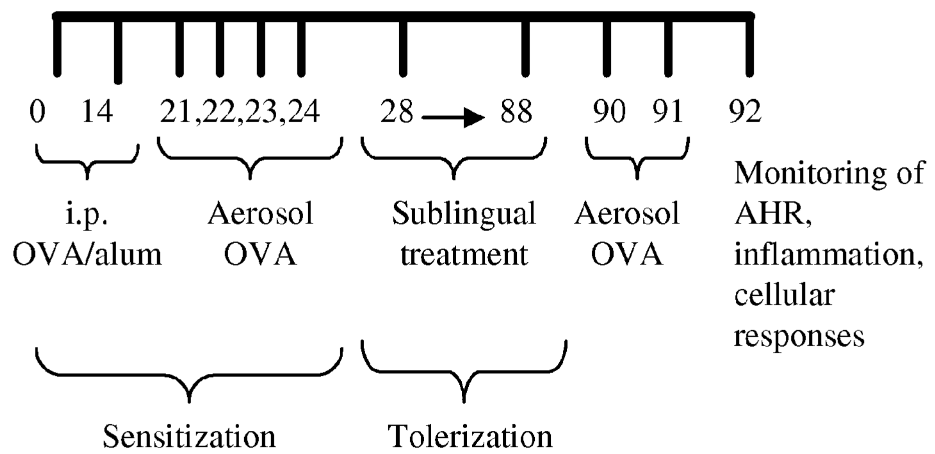
Figure 13:
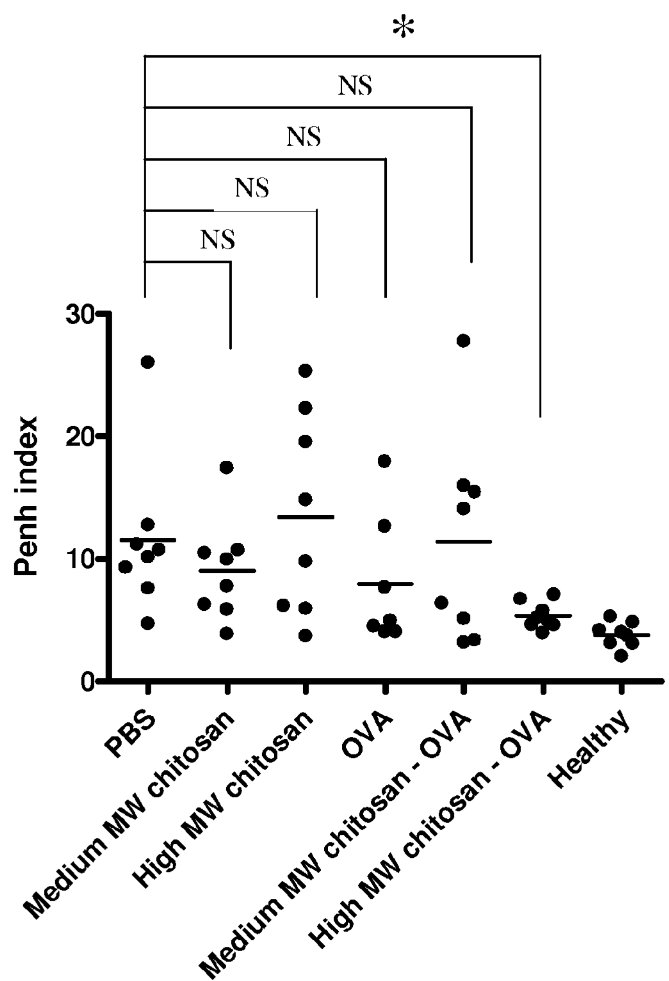

Therapeutic SLIT with high MW chitosan-formulated OVA, not with medium MW chitosan-formulated OVA, reduces established AHR, lung inflammation and OVA-specific Th2 responses in mediastinal LNs. All mice were sensitized by intraperitoneal injections with OVA/alum followed by an aerosol challenge (FIG. 12). BALB/c mice were then sublingually treated with PBS, OVA, chitosan-formulated OVA (high or medium MW) or chitosan alone. After OVA aerosol challenges, AHR, lung inflammation and cellular responses were investigated. AHR was determined by measuring the Penh index of all groups of mice (FIG. 13) (-=mean). *$p<0.05$ compared with PBS-desensitized mice, NS: Not significant. n=7 to 8. For tissue histology (FIG. 14), representative paraffin lung sections stained with HES from mice desensitized with either PBS, OVA, high MW chitosan-formulated OVA or chitosan alone are shown (100-fold magnification). Eosinophils were counted in BAL collected from mice treated with PBS, OVA, high MW chitosan-formulated OVA or chitosan alone (FIG. 15). Mean+/−SE. n=7 to 8. *$p<0.05$ compared with PBS-desensitized mice, NS: Not significant. For LNs responses analysis, IL-13, IL-5 and IL-10 secretions in mediastinal (FIG. 16, FIG. 17, FIG. 18) and cervical (FIG. 19) LNs were measured by CBA assay. Mean+/−SE. n=6 to 8.

EXAMPLES

Animals, Culture Medium, Reagents and Formulations 6-week-old female BALB/c mice were purchased from Charles River (L'Arbresle, France) and maintained on an OVA-free diet. DO11.10 OVA-specific T cell receptor (TCR) transgenic female mice with approximately 50% of their CD4+ T cells expressing a TCR specific for the peptide 323-339 fragment of OVA (Murphy et al. Science 1990; 250:1720-1723), were bred in the Centre d'Exploration et de Recherche Fonctionnelle Expérimentale (Evry, France). International levels of ethical standards for the manipulation of animals were applied.

Complete medium for LNs cells culture, bone marrow-derived dendritic cells (BMDCs), oral dendritic cells (DCs), and OVA-specific T cells from DO11.10 mice consisted of RPMI 1640 supplemented with 10% fetal calf serum, 1% L-glutamine, 200 U/ml penicillin, and 200 μg/ml streptomycin (all from Invitrogen, Carlsbad, Calif.). Recombinant murine GM-CSF and IL-4 were obtained from Gentaur (Brussels, Belgium). Phosphate-buffered saline (PBS) and alum were purchased from Lonza (Basel, Switzerland) and Pierce (Rockford, Ill.), respectively. OVA grade V with low endotoxin content was purchased from Sigma (St. Louis, Mo.) and was further purified on an endotoxin removing gel (Pierce) as described before (10). Residual endotoxin concentrations determined by Endochrom-K assay (R1708K, Charles River, Wilmington, Mass.) were always less than 0.1 EU/μg protein.

In the following, mean comparisons were performed using Student's t-tests. A p value $<0.05$ was considered as statistically significant.

Example 1

Characterization of Chitosan Particles

Particles were prepared from both high and medium MW chitosan, which differ in the chain length of the polymer.

Briefly, to prepare OVA-loaded chitosan particles, 0.05 g of chitosan, with either high or medium molecular weight (MW) (419419 or 448877 from Sigma, respectively), was dissolved in 25 ml aqueous acetic acid solution (1%). The suspension was homogenized with a Ultra Turrax T18 homogeneizer (Ika, Staufen, Germany) at 9500 rpm for 2 min, and the pH was adjusted to 5 with a solution of NaOH 1 N. Then 30 ml of a 20 mg/ml OVA solution was added at 0.75 ml/min under magnetic stirring at room temperature, and cross-linking was performed after adding 10 ml of a 0.1% tripolyphosphate aqueous solution (Sigma).

Size and charge (zeta potential) of chitosan particles were analysed using a Zetasizer Nano ZS (Malvern, Worcestershire, UK). The size of high MW chitosan- and medium MW chitosan-OVA particles were 1.0-3.0 μm, and 300-800 nm, respectively. High MW chitosan- and medium MW chitosan-OVA particles exhibited a zeta potential of 7.3+/−0.9 mV and 1.8+/−0.6 mV, respectively.

To verify the antigenicity of OVA formulated in chitosan, the capacity of OVA alone or chitosan-formulated OVA to bind OVA-specific antibodies was measured using an ELISA inhibition test with sera from OVA-immunized mice.

Purified OVA (0.2 μg) was coated overnight at 4° C. onto ELISA plates (Nunc, Roskilde, Denmark). After washing and blocking steps, sera from OVA-immunized mice (1/5000) and OVA or chitosan-formulated OVA dilutions (1/2 to 1/800000) were added and incubated for 2 h30 at room temperature. Plates were washed, peroxidase-conjugated sheep anti-mouse IgG antibodies (dilution 1/1000, Sigma) were added for 1 hour at 37° C., and orthophenylenediamine (OPD) was used as a substrate (Sigma). The reaction was stopped with 2 M sulfuric acid and optical densities determined using an ELISA plate reader at 492 nm (Labsystems, Helsinki, Finland).

Figure 1:
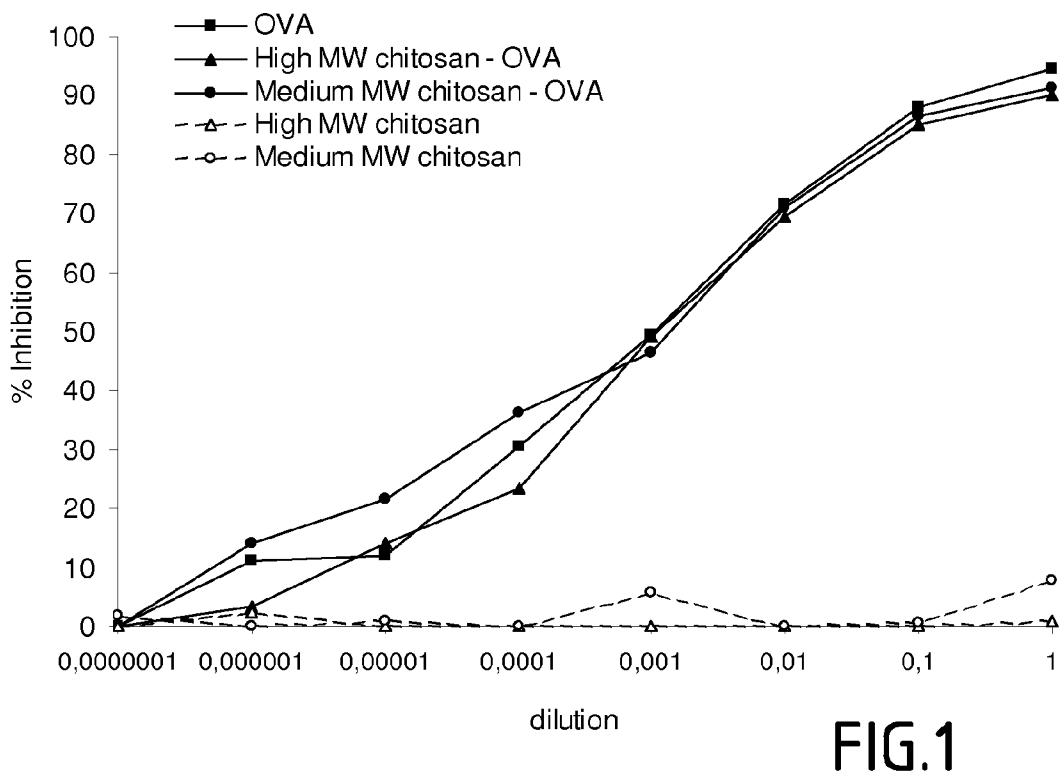
FIG. 1

As shown in FIG. 1, OVA formulated in either high or medium MW chitosan particles remained well recognized by specific antibodies.

Example 2

Chitosan Particles Improve OVA Uptake and Processing by Dendritic Cells

To investigate the effect of chitosan particles on allergen uptake, in vitro studies were performed using fluorescein isothiocyanate (FITC) labelled-OVA and chitosan-formulated FITC-OVA.

BMDCs were generated from femurs and tibiae from 6- to 8-week-old BALB/c mice as previously described (Inaba et al. J Exp Med 1992; 176:1693-1702), and confirmed to express CD11c (with purity >90%) by flow cytometry analysis (FC500 Flow Cytometer, Beckman Coulter, Villepinte, France). For antigen uptake assays, cells were suspended at 5×104/ml in complete medium. FITC-labelled OVA or chitosan-formulated FITC-OVA were added at a final concentration of 25 μg/ml, and cells were incubated for 15 min, 1 h or 4 h, at 37° C. or 4° C.

Figure 2:
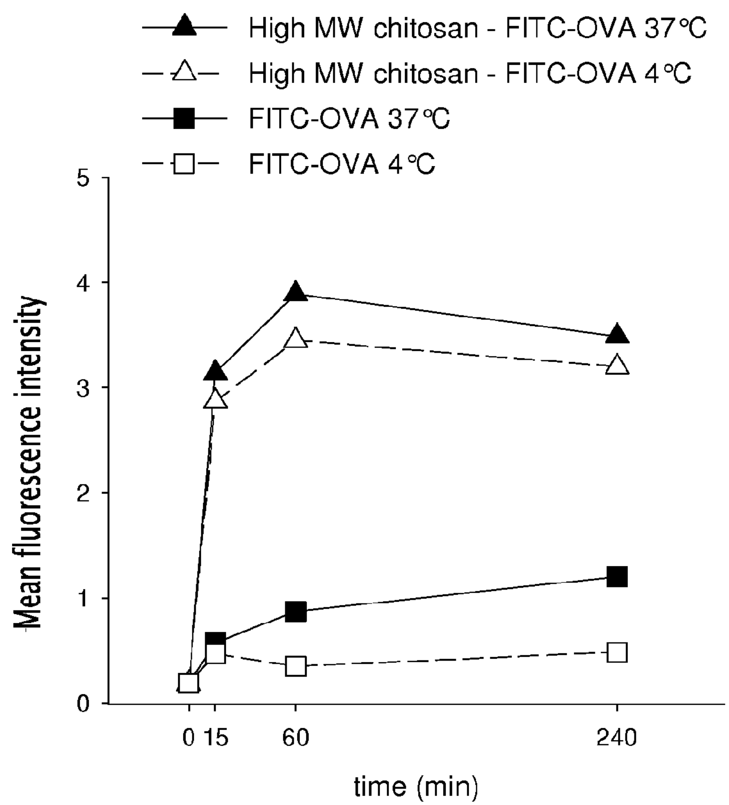
Figure 3:
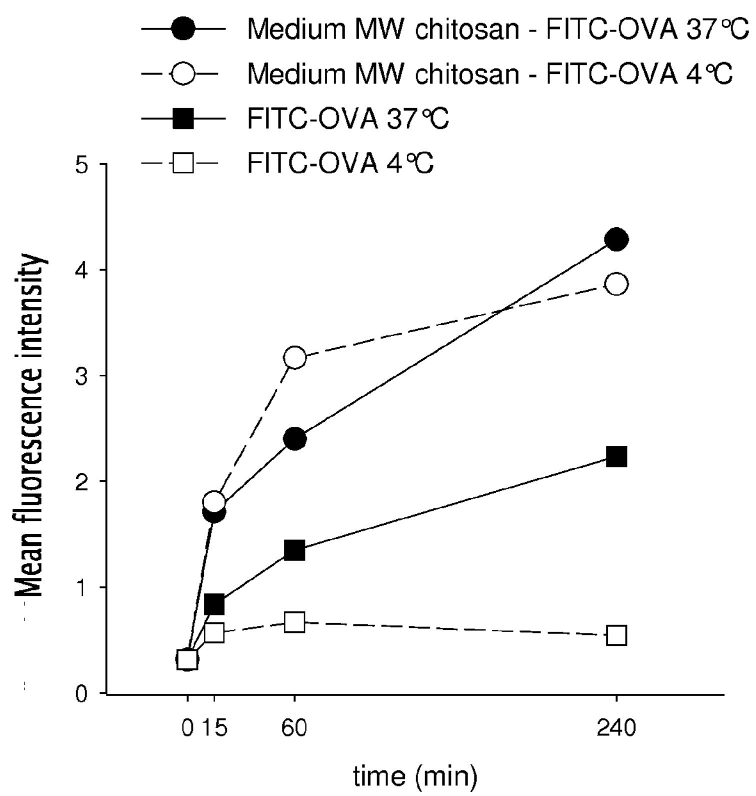

As shown in FIGS. 2 and 3, both high and medium MW chitosan particles dramatically enhanced OVA uptake by BMDCs when compared to soluble OVA. Of note, a similar fluorescence was detected with chitosan-formulated FITC-OVA at 4° C.

In vitro processing assays by BMDCs were realized using DQ-OVA (Invitrogen) and chitosan-formulated DQ-OVA which fluoresces after proteolytic cleavage. Briefly, 5×104/ml cells were suspended in complete medium, and 10 μg/ml DQ-OVA or chitosan-formulated DQ-OVA was added for 3 h at 37° C. or 4° C. For both experiments, cells were then washed two times with cold HBSS and analysed by flow cytometry. Results were expressed as mean fluorescence intensity.

Figure 4:
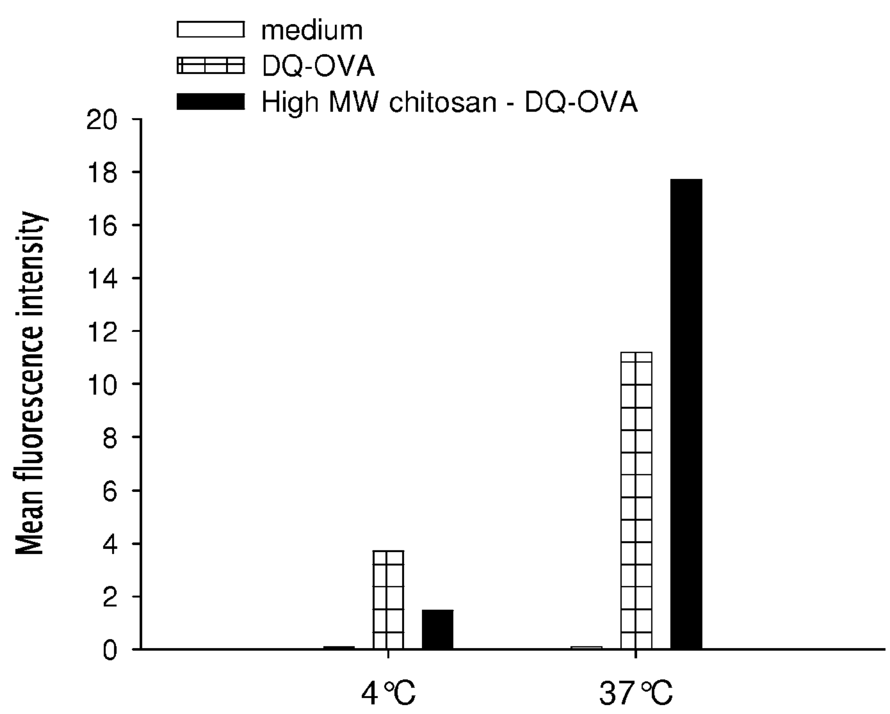
Figure 5:
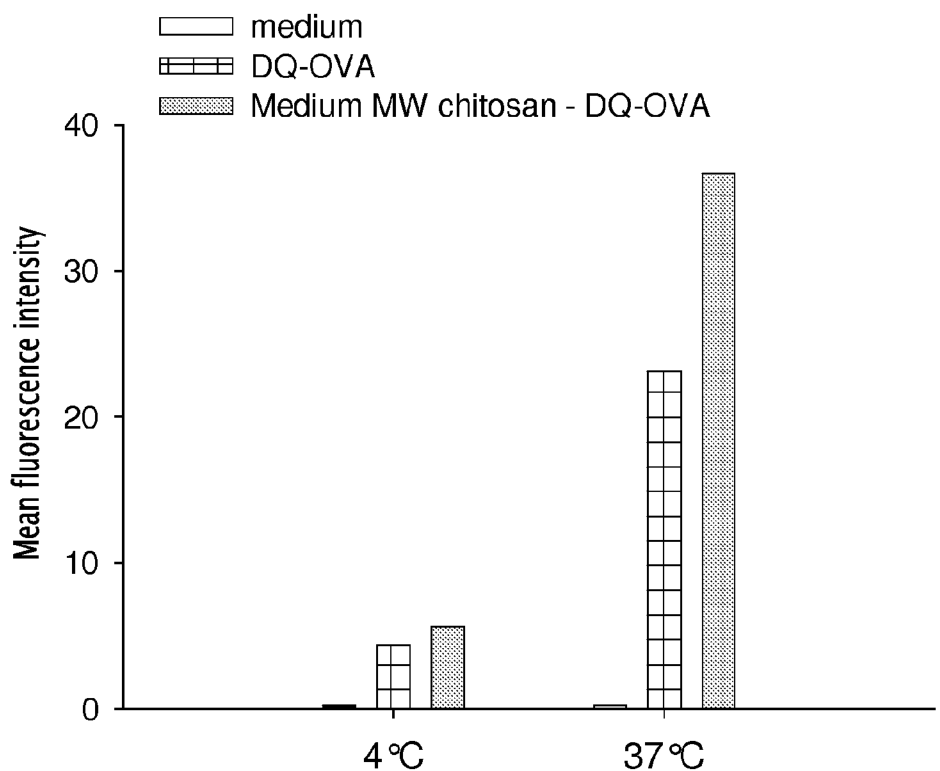

As presented in FIGS. 4 and 5, both chitosan particles significantly improved OVA processing by BMDCs when compared to soluble OVA.

To further investigate chitosan-formulated OVA uptake by APCs, the inventors used myeloid CD11b+ CD11c− murine DCs isolated from oral tissues.

Briefly, buccal floor and lingual tissues were removed from naïve BALB/c mice, and treated for 45 min at 37° C. with 400 U/ml collagenase type IV (Roche diagnostic, Mannheim, Germany), 50 μg/ml DNase I (Roche diagnostic) and 2 U/ml dispase (Invitrogen) in RPMI. After blocking residual enzymatic activity with 5 mM EDTA in PBS, oral tissues were dissociated in PBS. Single cell suspensions were labelled with phycoerythrin (PE)-labelled anti-CD11b and allophycocyanin (APC)-labelled anti-CD11c antibodies (both from BD Biosciences, San Jose, Calif.). CD11b+ CD11c− cells, representing the main subset of oral dendritic cells, were isolated using a MoFlo (Dako, Glostrup, Denmark) cell sorter. Cells were more than 99% pure as assessed by flow cytometry analysis. Oral DCs (104/well in 100 μl complete medium) were incubated with either DQ-OVA or chitosan-formulated DQ-OVA at a final concentration of 10 μg/ml. After 1 h at 37° C. or 4° C., cells were washed and analysed by flow cytometry. Results were expressed as mean fluorescence intensity.

Figure 6:
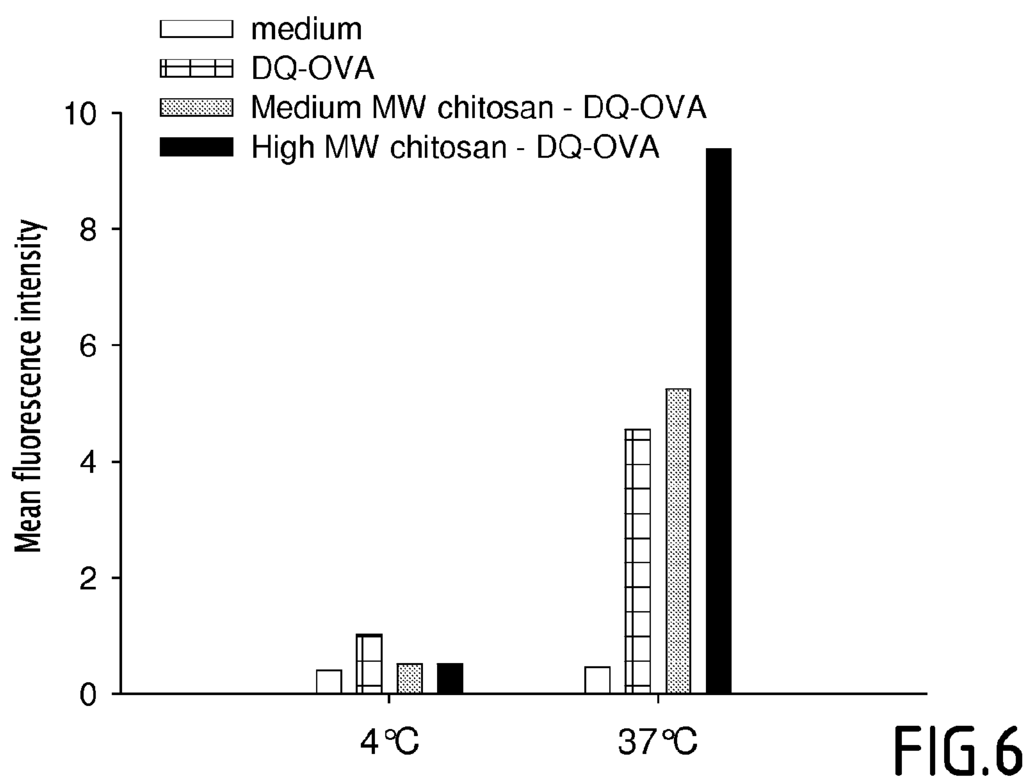

As shown in FIG. 6, only high MW chitosan-formulated OVA enhanced OVA processing by oral DCs.

Example 3

High MW Chitosan-Formulated O'VA Enhances In Vitro T Cell Proliferation and IFN-γ/IL-10 Secretion To determine whether the superior uptake of chitosan-formulated OVA by DCs improved subsequent T cell proliferation and cytokine secretion, OVA-specific CD4+ naïve T lymphocytes from DO11.10 mice were labelled with carboxyfluorescein diacetate succinimidyl ester (CFSE) and co-cultured with BMDCs and either medium alone, OVA, chitosan alone, or chitosan-formulated OVA.

Briefly, CD4+ T cells were purified from spleens of DO11.10 mice by magnetic bead separation using a mouse CD4 negative isolation kit (Invitrogen) according to the manufacturer's instructions. Resulting T cell preparations contain 95-99% naïve CD4+ T cells (subsequently termed DO11.10 T cells). DO11.10 T cells were labeled with 1 μM CFSE (Invitrogen) for 5 min at 37° C. in PBS and washed twice. CFSE-labelled DO11.10 T cells were then incubated (in duplicate) with BMDCs and either OVA (1.5 or 15 μg/ml), chitosan-formulated OVA (1.5 or 15 μg/ml), or chitosan alone for 3 days. OVA-specific T cells were stained with the anti-clonotypic PE-KJ1.26 mAb (BD Biosciences) and proliferating T cells were evaluated by flow cytometry analysis, as cells with a decreased CFSE-associated fluorescence.

IL-5, IL-10 and IFN-γ were measured in culture supernatants (corresponding to 15 μg/ml OVA concentrations) using a Cytometric Bead Array (CBA) Flex kit (BD Biosciences). Measurements were made in comparison with a 10-point standard curve obtained by serial dilutions of the reconstituted lyophilized standards. A reagent mixture was obtained by mixing 10 μl of each murine capture bead suspension. This mixture was vigourously vortexed and incubated in the dark for 90 min at room temperature with either test samples or standard dilutions. 50 μl of the phycoerythrin (PE)-labelled detection reagent were then added to each well and incubated in the dark for 2 h at room temperature. Beads were washed, resuspended in 200 μl buffer and analysed by flow cytometry according to the manufacturer's instructions.

Figure 10:
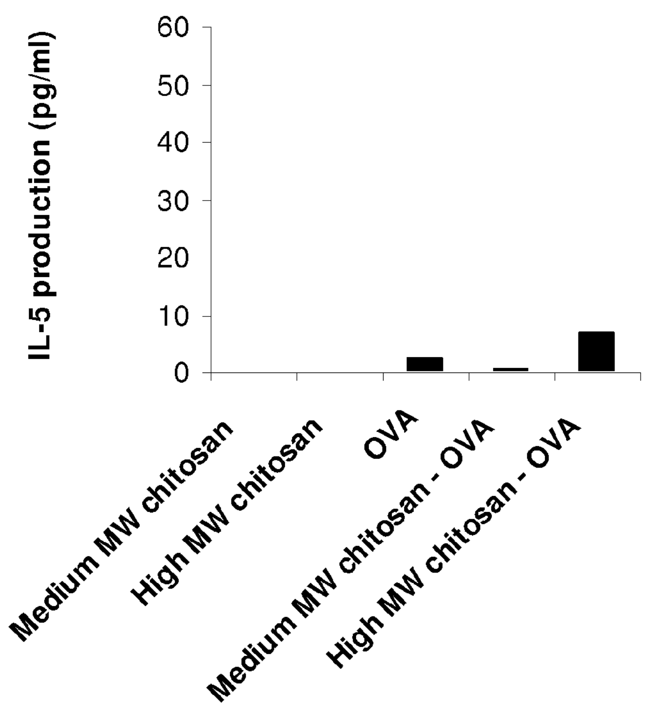

As shown in FIG. 7, targeting DCs with high MW chitosan-formulated OVA enhanced T-cell proliferation compared with OVA alone. This was associated with a dramatic increase in IFN-γ (FIG. 8) and IL-10 (FIG. 9) secretion by T cells, whereas no impact on IL-5 secretion was observed (FIG. 10). Incubation with medium MW chitosan-formulated OVA induced a lower T cell proliferation (FIG. 7), as well as little IFN-γ and IL-10 secretions (FIGS. 8 and 9) when compared to soluble OVA. No detectable changes in IL-5 secretions were observed (FIG. 10). No cytokine secretion was detected in absence of DO11.10 CD4+ T cells.

Example 4

T Cell Priming Occurs in Cervical LNs After Sublingual Administration of High MW Chitosan-Formulated OVA To assess whether chitosan-OVA particles could enhance T cell priming in draining LNs following sublingual administration, OVA-specific DO11.10 CD4+ T cells CFSE-labelled as described above were adoptively transferred into BALB/c mice before SLIT.

Briefly, 5×106 cells were adoptively transferred by retro-orbital intravenous injection into BALB/c mice at day 0. Twenty-four hours later, mice (3 to 5 mice per group) were treated by the sublingual route with either soluble OVA or chitosan-formulated OVA (500 μg OVA per dose). Control animals were treated with either sterile PBS or chitosan formulations alone. Cervical LNs were recovered at day 10. OVA-specific T cells were stained with the anticlonotypic PE-KJ1.26 mAb (BD Biosciences) and proliferating cells were evaluated by flow cytometry analysis as cells with decreased fluorescence.

Figure 11:
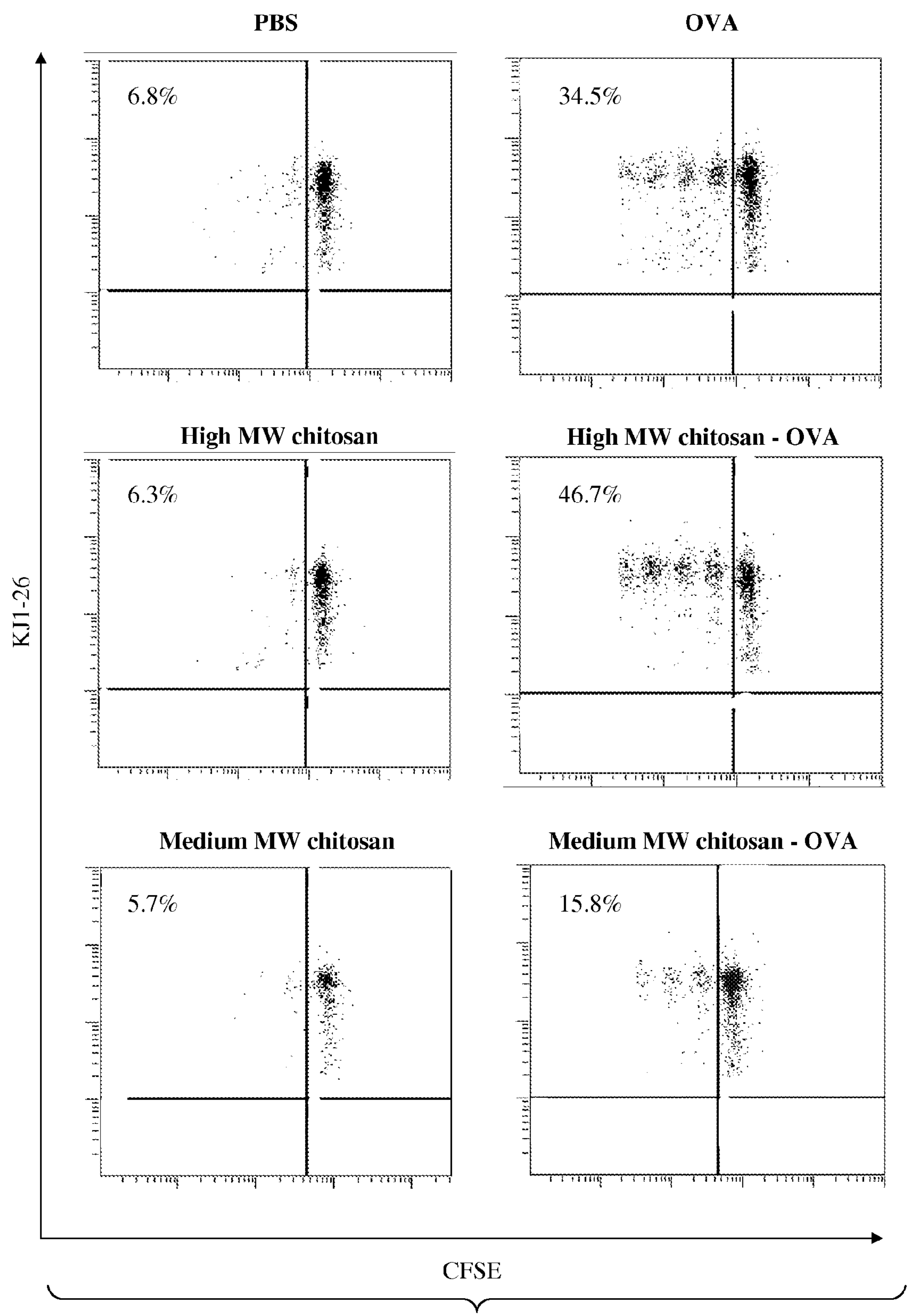

As shown in FIG. 11, T cell proliferation was hardly detectable in cervical LNs of mice sublingually treated with either PBS, high MW chitosan or medium MW chitosan, with only 6.8%, 6.3%, and 5.7% proliferating T cells, respectively. In contrast, sublingual administration of OVA induced a readily detectable T cell proliferation in cervical LNs, in the range of 34.5%. Interestingly, the use of high MW chitosan-formulated OVA strongly enhanced T cell proliferation (with up to 46.7% proliferating T cells), whereas medium MW chitosan-formulated OVA induced a lower (15.8%) T cell proliferation when compared with OVA alone.

Example 5

Therapeutic Sublingual Treatment with High MW Chitosan-Formulated OVA Reduces Established AHR Given the evidence that chitosan particles could be used to target the antigen onto DCs, they were tested in a murine SLIT model relying upon mice sensitized with OVA (Razafindratsita et al. J Allergy Clin Immunol 2007; 120:278-285). Those mice exhibit severe airway hyperresponsiveness (AHR), lung inflammation characterized by a high cellular infiltration and mucus hyperproduction, and systemic OVA-specific Th2 immune responses.

Briefly, BALB/c mice sensitization was performed by two intraperitoneal (i.p.) injections at 14 days intervals with 10 μg OVA adsorbed onto 2 mg Al(OH)3 administered in a volume of 100 μl. This was followed by a 20 min aerosol challenge with 1% w/v OVA on 4 consecutive days using an aerosol delivery system (Buxco Europe Ltd, Winchester, UK). Mice were then treated sublingually twice a week during 2 months, by applying solutions (OVA or chitosan-formulated OVA, 500 μg per dose) under the tongue, while holding animals on their back (for 1 minute) to prevent swallowing (FIG. 12). Control animals were sham-desensitized with sterile PBS or chitosan formulations alone. Two days after treatment, mice were challenged with OVA aerosols (1% w/v) on 2 consecutive days.

Measurements of AHR were performed 24 h after the last challenge by whole body plethysmography (Buxco) as described elsewhere (Hamelmann et al. Am J Respir Crit Care Med 1997; 156:766-775). Airway resistance was expressed as enhanced pause (Penh). A Penh index, expressed as an increase relative to the baseline airway resistance, was obtained by dividing the Penh measured after exposure to 100 mg/ml inhaled metacholine with the Penh measured after inhalation of nebulized PBS.

High MW chitosan-formulated OVA treatment dramatically reduced AHR (FIG. 13), leading to Penh index values comparable to the ones from healthy nonsensitized mice, whereas soluble OVA treatment had a moderate effect on AHR. Conversely, treatment with medium MW chitosan-formulated OVA had no beneficial effect on AHR. Noteworthy, chitin particles co-administered with OVA did not reduce AHR more than OVA alone.

Example 6

Therapeutic Sublingual Treatment with High MW Chitosan-Formulated OVA Reduces Bronchial Inflammation Bronchial inflammation was subsequently assessed in all groups For tissue histology, lungs were recovered and fixed in phosphate buffered formalin-zinc and embedded in paraffin wax. Sections were stained with hematoxylin, eosin and safran (HES) for the determination of cellular infiltrates. A semi-quantitative assessment of perivascular, peribronchial, and alveolar inflammation was performed on coded samples.

For the analysis of inflammatory cells within broncho-alveolar lavages (BAL), mice were anesthetized 24 h after the last OVA challenge by an i.p. injection of a pentobarbital solution (50 mg/kg body weight). The BAL was then performed with 600 μl PBS. The BAL fluid was centrifuged at 800 g for 10 min at 4° C. Cell pillets were resuspended in PBS, spun onto glass slides by cytocentrifugation, and then fixed and visualized after May-Grünwald Giemsa staining (Réactifs RAL, Martillac, France). Eosinophils were counted by light microscopy at ×200 magnification.

Figure 14:
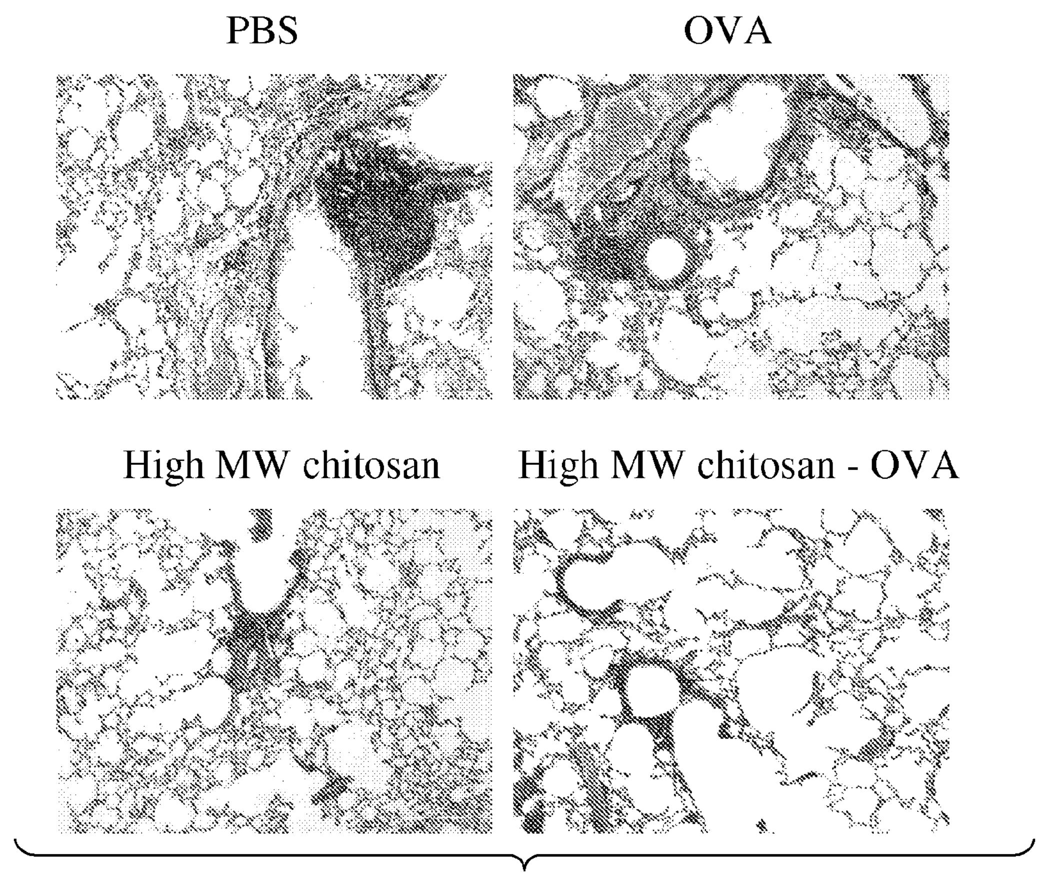
Figure 15:
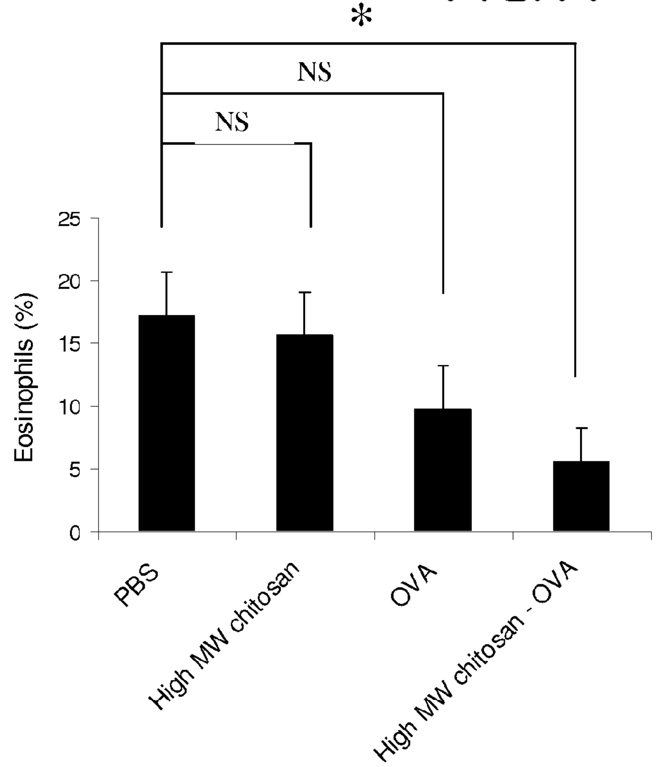
Figure 16:
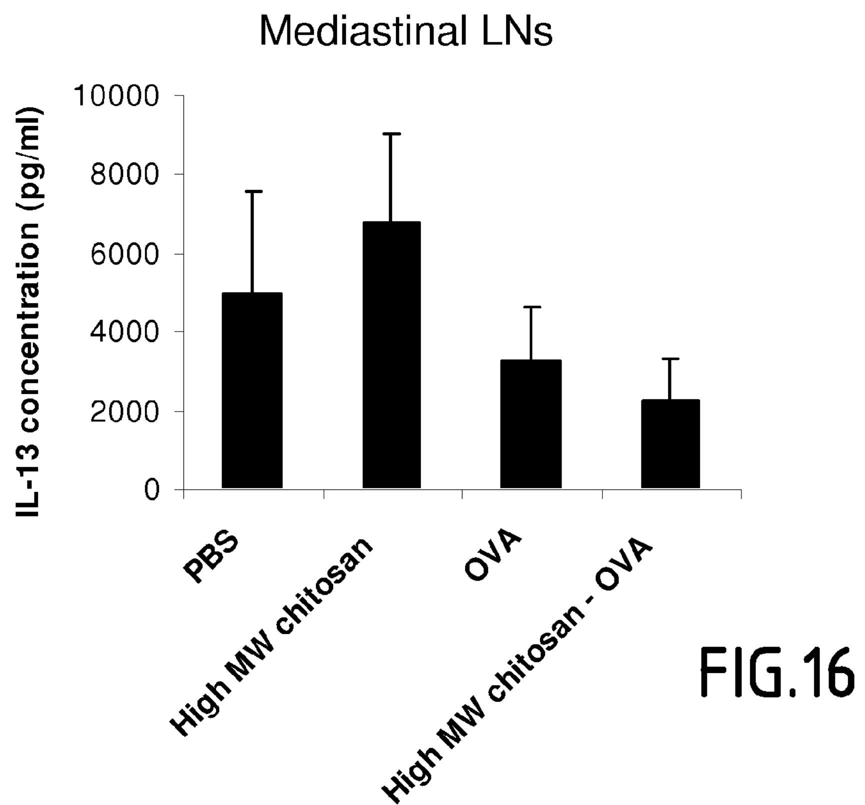
Figure 17:
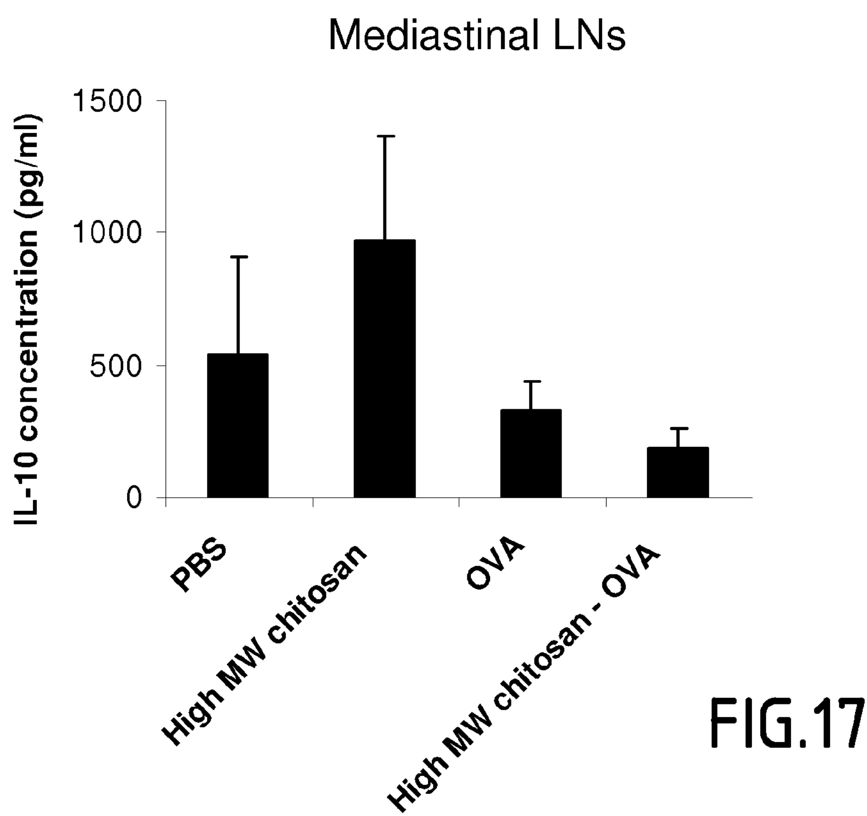
Figure 18:
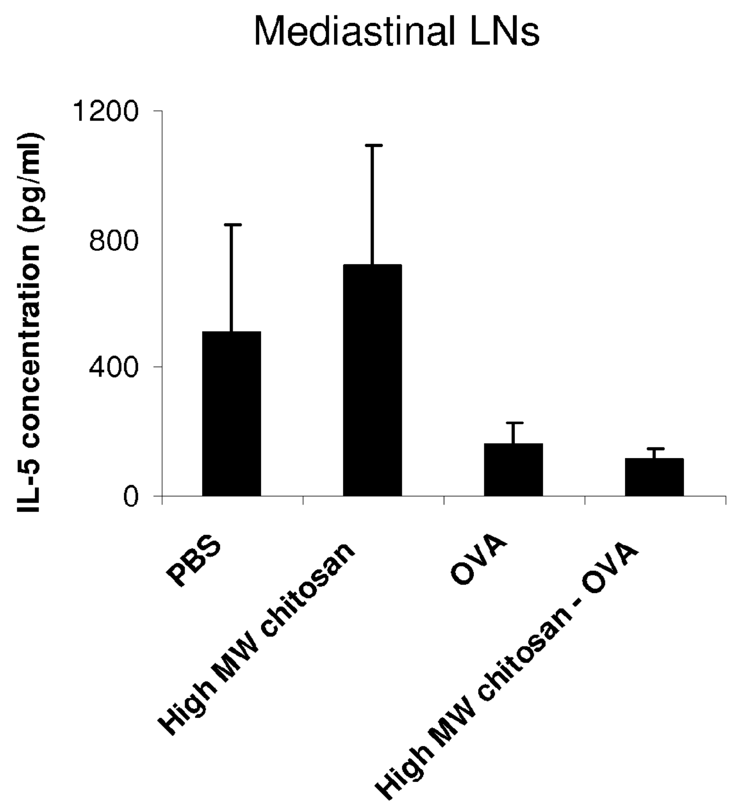

The observed decrease of AHR after treatment with high MW chitosan-formulated OVA was associated with a reduction in bronchial inflammation and cellular infiltrates as shown by the analysis of lung tissue sections (FIG. 14 and Table 1).

TABLE 1

Therapeutic SLIT with high MW chitosan-formulated OVA reduces perivascular, peribronchial, and alveolar inflammation.
Lungs from mice treated with PBS, OVA, high MW chitosan-formulated OVA or chitosan alone were removed, fixed, and stained with HES for the determination of cellular infiltrates. A semi-quantitative assessment of perivascular, peribronchial, and alveolar inflammation was performed on coded samples. Data are expressed as numbers of animals exhibiting signs of inflammation

| | | Perivascular inflammation | | | Peribronchial inflammation | | | Alveolar inflammation | | |
|---|---|---|---|---|---|---|---|---|---|---|
| Groups | n | − | + | ++ | − | + | ++ | − | + | ++ |
| PBS | 7 | 1/7 | 5/7 | 1/7 | 1/7 | 5/7 | 1/7 | | 4/7 | 3/7 |
| OVA | 7 | 4/7 | 3/7 | | 4/7 | 3/7 | | 1/7 | 6/7 | |
| Chitosan | 8 | 2/8 | 6/8 | | 2/8 | 6/8 | | 3/8 | 5/8 | |
| Chitosan + OVA | 8 | 7/8 | 1/8 | | 7/8 | 1/8 | | 6/8 | 2/8 | |

This reduction in bronchial inflammation was correlated with a significant reduction in eosinophil counts in BAL compared to treatment with OVA alone (FIG. 15).

Example 7

Therapeutic Sublingual Treatment with High MW Chitosan-Formulated OVA Reduces OVA-Specific Th2 Responses in Mediastinal LNs Immune responses in mediastinal and cervical LNs were subsequently assessed in all groups.

For T cell responses assessment, mediastinal and cervical LNs were removed, cells were isolated, plated at 3×105 cells per well, and stimulated with OVA (100 μg/ml) or medium alone. Plates were incubated for 72 hours at 37° C. in 5% CO2/95% air. IL-5, IL-10 and IFN-γ were measured in culture supernatants using a CBA Flex kit, as described above.

Figure 19:
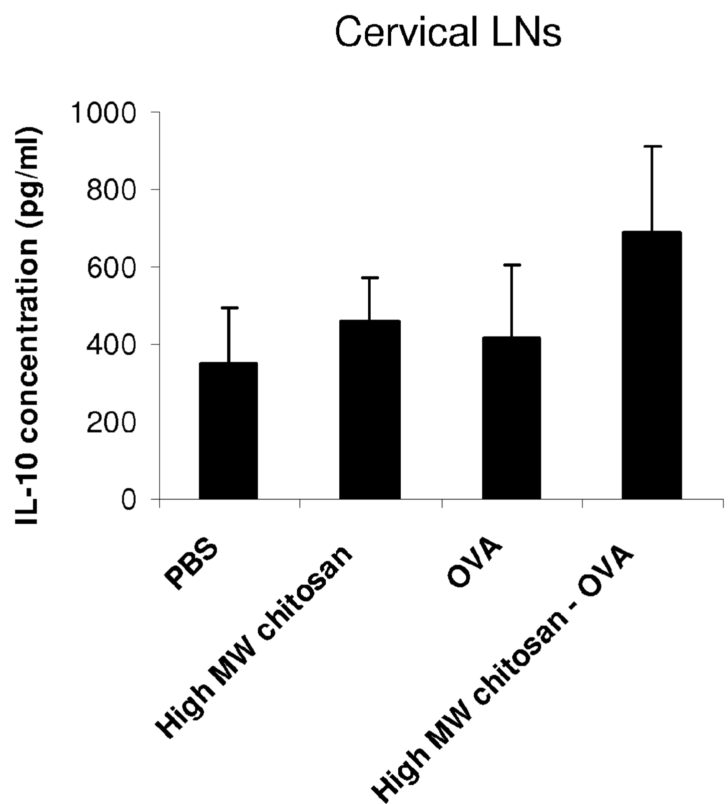

Mice treated with high MW chitosan-formulated OVA exhibited slightly lower OVA-specific IL-13 (FIG. 16), IL-10 (FIG. 17) and IL-5 (FIG. 18) production in mediastinal LNs, compared to OVA alone. In contrast, higher IL-10 levels were detected in cervical LNs, whereas no variation in any of the Th2 cytokines was observed (FIG. 19). No changes in IFN-γ secretion and serum OVA-specific IgE or IgG antibodies were observed in any of the groups (data not shown).

The invention claimed is:

1. A method for treating allergy by enhancing the induction of a specific tolerance towards at least one allergen involved in said allergy, comprising:

administering, by the mucosal route, to an individual suffering from said allergy, a therapeutically effective quantity of a mucoadhesive composition comprising chitosan particles loaded with the at least one allergen involved in the allergy, said allergen being a protein, polypeptide or peptide, wherein the size of the loaded chitosan particles is from 1 μm to 3 μm and the chitosan particles are made of chitosan which viscosity is at least 800 cP, wherein the chitosan particles of the mucoadhesive composition enhance the induction of the specific tolerance towards the at least one allergen involved in said allergy, and wherein said allergen is selected from the group consisting of pollen allergens, mite allergens, insect allergens, animal hair and dandruff allergens, and food allergens.

2. The method according to claim 1, wherein the zeta potential of the loaded chitosan particles is more than 2.5 mV.

3. The method according to claim 1, wherein the zeta potential of the loaded chitosan particles if from 6 to 9 mV.

4. The method according to claim 1, wherein the mucoadhesive composition is in association with a pharmaceutically acceptable carrier in an immunotherapeutic composition.

5. The method according to claim 4, wherein the immunotherapeutic composition is in the form of a suspension, a gel, a powder, a tablet, a capsule, or a lyoc.

6. The method according to claim 4, wherein the immunotherapeutic composition further comprises an adjuvant for enhancing antigen-specific tolerance induction.

7. The method according to claim 1, wherein the mucoadhesive composition is administered via the oromucosal route.

8. The method according to claim 1, wherein the mucoadhesive composition is administered via the sublingual route.

9. A method for enhancing the induction, in an individual suffering from allergy, of a specific tolerance towards at least one allergen involved in said allergy, said allergen being a protein, polypeptide or peptide, comprising:

administering to said individual, by the mucosal route, a therapeutically effective quantity of a mucoadhesive composition comprising chitosan particles loaded with the at least one allergen involved in the allergy, wherein the size of the loaded chitosan particles is from 1 μm to 3 μm and the chitosan particles are made of chitosan which viscosity is at least 800 cP, wherein chitosan particles of the mucoadhesive composition enhance the induction of a specific tolerance towards the at least one allergen involved in said allergy, and wherein said allergen is selected from the group consisting of pollen allergens, mite allergens, insect allergens, animal hair and dandruff allergens, and food allergens.

10. The method according to claim 9, wherein said at least one allergen involved in said allergy is selected from the group consisting of Bet v I, Bet v II, Blo t I, Blo t III, Blo t V, Blo t XII, Cyn d I, Der p I, Der p II, Der P III, Der p VII, Der f I, Der f II, Der f III, Der f VII, Fe; d I, Amb a I.1, Amb a I.2, Amb a 1.3, Amb a 1.4, Amb a II, Lol p I, Lol p II, Lol p III, Lol p IV, Lol p IX, Lol p V, Lol p Ib, Cry j I, Cry j II, Can f I, Can f II, Jun s I, Jun v I, Jun a I, Jun a II, Dac g I, Dac g V, *Poa* p I, Phl p I, Phl p V, Phl p VI and Sor h I.

* * * * *